United States Patent
Navve et al.

(10) Patent No.: US 9,265,581 B2
(45) Date of Patent: Feb. 23, 2016

(54) RELAY BASED TOOL CONTROL

(71) Applicant: Gyrus ACMI, Inc., Southborough, MA (US)

(72) Inventors: Adi Navve, Kfar Saba (IL); Shai Finkman, Haifa (IL); Doron Adler, Haifa (IL)

(73) Assignee: Gyrus ACMI, Inc., Southborough, MA (US)

( * ) Notice: Subject to any disclaimer, the term of this patent is extended or adjusted under 35 U.S.C. 154(b) by 15 days.

(21) Appl. No.: 14/251,605

(22) Filed: Apr. 13, 2014

(65) Prior Publication Data

US 2014/0316433 A1    Oct. 23, 2014

Related U.S. Application Data

(63) Continuation-in-part of application No. 13/933,144, filed on Jul. 2, 2013.

(60) Provisional application No. 61/814,278, filed on Apr. 21, 2013.

(51) Int. Cl.
*A61B 19/00* (2006.01)
*A61B 17/00* (2006.01)
*A61B 17/29* (2006.01)

(52) U.S. Cl.
CPC ....... *A61B 19/22* (2013.01); *A61B 2017/00212* (2013.01); *A61B 2017/291* (2013.01); *A61B 2019/2296* (2013.01); *A61B 2019/266* (2013.01)

(58) Field of Classification Search
CPC ............... A61B 2019/2296; A61B 2019/266; A61B 2017/291; A61B 2017/00212; A61B 19/22; A61B 2019/40268; A61B 2019/40399; G05B 2219/40268; G05B 2219/40399

USPC ........................................................ 606/130
See application file for complete search history.

(56) References Cited

U.S. PATENT DOCUMENTS 5,275,608 A    1/1994  Forman et al.
5,520,678 A    5/1996  Heckele et al.
(Continued)

FOREIGN PATENT DOCUMENTS

EP    1847223 A1    10/2007
EP    2064985 A3    6/2009
(Continued)

OTHER PUBLICATIONS

International Application PCT/US14/33903 Search Report dated Sep. 17, 2014.
(Continued)

*Primary Examiner* — Khoi Tran
*Assistant Examiner* — Robert Nguyen
(74) *Attorney, Agent, or Firm* — D.Kligler IP Services Ltd.

(57) ABSTRACT

Medical apparatus, including a local medical tool and a remote medical tool, located remotely from the local medical tool. The apparatus includes a lockable joint, physically connected to the local medical tool, that is operable in a locked state or in an unlocked state. A handle is physically connected to the lockable joint, so that in the locked state of the joint, movements of the handle are directly transferred to corresponding movements of the local medical tool. The apparatus includes sensors that are configured, in the unlocked state of the joint, to measure motions of the handle with respect to the lockable joint. The apparatus also includes a controller, which in the unlocked state of the joint receives indications of the motions of the handle with respect to the lockable joint, and which is configured to apply the indications to generate corresponding motions for the remote medical tool.

20 Claims, 5 Drawing Sheets

(56) References Cited

U.S. PATENT DOCUMENTS

| | | |
|---|---|---|
| 6,451,027 B1 | 9/2002 | Cooper et al. |
| 6,558,407 B1 | 5/2003 | Ivanko et al. |
| 7,778,733 B2 | 8/2010 | Nowlin et al. |
| 7,927,271 B2 | 4/2011 | Dimitriou et al. |
| 2002/0120252 A1 | 8/2002 | Brock et al. |
| 2002/0128552 A1 | 9/2002 | Nowlin et al. |
| 2003/0060808 A1 | 3/2003 | Wilk |
| 2004/0044279 A1 | 3/2004 | Lewin et al. |
| 2004/0267089 A1 | 12/2004 | Otsuka et al. |
| 2006/0116667 A1 | 6/2006 | Hamel et al. |
| 2006/0201130 A1* | 9/2006 | Danitz ............... A61B 17/2909 59/78.1 |
| 2007/0095355 A1* | 5/2007 | Oomori ............... A61B 17/062 128/898 |
| 2007/0137372 A1 | 6/2007 | Devengenzo et al. |
| 2007/0282371 A1 | 12/2007 | Lee et al. |
| 2008/0167522 A1* | 7/2008 | Giordano ............. A61B 19/026 600/104 |
| 2008/0167736 A1* | 7/2008 | Swayze ............ A61B 17/07207 700/83 |
| 2008/0188870 A1* | 8/2008 | Andre et al. ................. 606/130 |
| 2009/0171371 A1 | 7/2009 | Nixon et al. |
| 2010/0228265 A1 | 9/2010 | Prisco |
| 2011/0022229 A1 | 1/2011 | Jang et al. |
| 2011/0028992 A1 | 2/2011 | Geiger et al. |
| 2011/0112517 A1 | 5/2011 | Peine et al. |
| 2011/0118748 A1 | 5/2011 | Itkowitz |
| 2011/0295270 A1* | 12/2011 | Giordano ........... A61B 19/2203 606/130 |
| 2012/0116391 A1 | 5/2012 | Houser et al. |
| 2013/0041292 A1 | 2/2013 | Cunningham |
| 2014/0005682 A1* | 1/2014 | Worrell et al. ................ 606/130 |
| 2015/0272572 A1* | 10/2015 | Overmyer ........... A61B 17/068 227/177.1 |

FOREIGN PATENT DOCUMENTS

| | | |
|---|---|---|
| JP | H06-054801 A | 3/1994 |
| JP | 2006061364 A | 3/2006 |
| WO | 9950721 A1 | 10/1999 |
| WO | 2007038998 A1 | 4/2007 |

OTHER PUBLICATIONS

Adler et al., U.S. Appl. No. 13/933,144, filed Jul. 2, 2013.
International Application PCT/US14/43060 Search report dated Sep. 30, 2014.
U.S. Appl. No. 13/933,144 Office Action dated Apr. 10, 2015.
U.S. Appl. No. 13/933,144 Office Action dated Sep. 16, 2015.

* cited by examiner

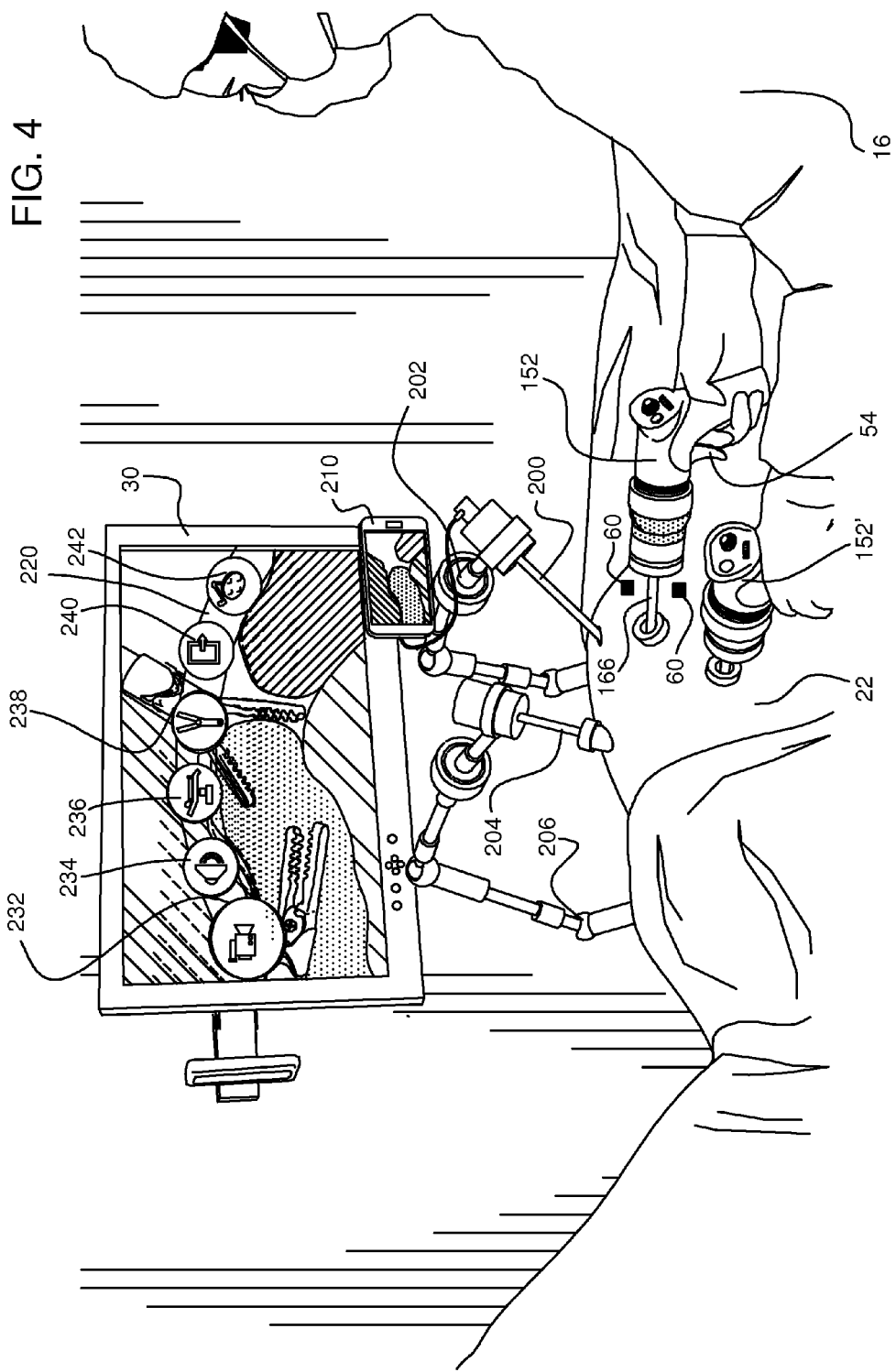

RELAY BASED TOOL CONTROL

CROSS-REFERENCE TO RELATED APPLICATIONS

The present application claims the benefit of U.S. Provisional Patent Application 61/814,278 filed 21 Apr. 2013, titled Relay Based Tool Control, which is incorporated herein by reference. The present application is a continuation-in-part of U.S. patent application Ser. No. 13/933,144, titled Robotic Surgery, which is incorporated herein by reference.

FIELD OF THE INVENTION

The present invention relates generally to manipulation of tools used for surgery, and specifically to local and remote manipulation of such tools.

BACKGROUND OF THE INVENTION

Many medical procedures are relatively intricate, requiring substantially simultaneous operation of numbers of complex pieces of equipment. In many cases the simultaneous operation is achieved by having two or even more physicians operating the equipment together, during a single procedure. Having more than one physician operating different pieces of equipment is expensive. In addition, a high level of communication between the different physicians is necessary in order for the multiple operations to be efficient.

SUMMARY OF THE INVENTION

An embodiment of the present invention provides medical apparatus, including:
 a local medical tool;
 a remote medical tool, located remotely from the local medical tool;
 a lockable joint, physically connected to the local medical tool, operable in a locked state or in an unlocked state;
 a handle, physically connected to the lockable joint, so that in the locked state of the joint, movements of the handle are directly transferred to corresponding movements of the local medical tool;
 sensors, configured, in the unlocked state of the joint to measure motions of the handle with respect to the lockable joint; and
 a controller, which in the unlocked state of the joint receives indications of the motions of the handle with respect to the lockable joint, and which is configured to apply the indications to generate corresponding motions for the remote medical tool.

Typically in the unlocked state the local medical tool is immobile.

At least one of the medical tools may include an endoscope.

In a disclosed embodiment the apparatus includes a selector, and the remote medical tool consists of multiple separate remote medical tools, each separate remote medical tool being located in a respective different position remote from the local medical tool, and the controller is configured to apply the indications to generate the corresponding motions for one of the separate remote medical tools selected by the selector.

In a further disclosed embodiment the handle includes controls which, in the locked state of the lockable joint, generate signals used by the controller to operate the local medical tool. Typically, the controls, in the unlocked state of the lockable joint, generate signals used by the controller to operate the remote medical tool.

The controls may include a magnification/demagnification regulator which provides a ratio, and the controller, in the locked state of the lockable joint, may apply the ratio to the movements of the handle with respect to the corresponding movements of the local medical tool. The controller, in the unlocked state of the lockable joint, may apply the ratio to the motions of the handle with respect to the corresponding motions of the remote medical tool.

In an alternative embodiment the apparatus includes a control connected to the handle, the control providing a motion consisting of at least one of a translation and a rotation, and the controller may be configured, in the unlocked state of the joint to apply the motion of the control to a corresponding motion of the remote medical tool, and in the locked state of the joint to apply the motion of the control to a corresponding movement of the local medical tool.

In a further alternative embodiment the sensors in the locked state of the joint are configured to measure selected motions of the handle with respect to the lockable joint, and the controller may receive respective indications of the selected motions, and may be configured to apply the respective indications to generate corresponding motions for the local medical tool.

There is further provided, according to an embodiment of the present invention a method, including:
 providing a local medical tool and a lockable joint connecting between the local medical tool and a handle, wherein the handle includes at least one sensor;
 providing a remote medical tool, located remotely from the local medical tool;
 sensing a motion of the handle with the at least one sensor; and
 applying indications of the sensed motion to generate a corresponding motion for the remote medical tool when the lockable joint is in an unlocked state.

In a disclosed embodiment, in a locked state of the lockable joint movements of the handle are directly transferred to corresponding movements of the local medical tool.

The present invention will be more fully understood from the following detailed description of the embodiments thereof, taken together with the drawings in which:

BRIEF DESCRIPTION OF THE DRAWINGS

FIG. 4 is a schematic illustration of the use of the tool handle of FIGS. 3A-3D during a medical procedure, according to an embodiment of the present invention.

DETAILED DESCRIPTION OF EMBODIMENTS

Overview

Embodiments of the present invention provide a system which enables a medical professional to single-handedly operate two or more tools used for performing a medical procedure, typically an invasive medical procedure. A handle is physically connected to a lockable joint, which is in turn physically connected to one of the tools, herein termed the "local" tool, used in the procedure. One or more other tools are positioned during the procedure remotely from the local tool. For simplicity, in this overview only one other tool, herein termed the "remote" tool, is assumed.

The system is configured to operate in two modes. In a locked mode of operation of the system, the joint connecting the handle to the local tool is locked, so that any movement of the handle is transferred directly to the local tool. In this mode the remote tool is maintained fixed in position with clamps, herein termed remote clamps.

In an unlocked mode of operation of the system, the joint connecting the handle to the local tool is unlocked, so that the handle is able to move with respect to the joint. In this mode the local tool is maintained fixed in its position with clamps (different from the remote clamps). However, in the unlocked mode, sensors detect motion of the handle with respect to the joint. A system controller receives signals from the sensors representative of the motion, and the controller uses the signals to alter the position of the remote clamps, so as to transfer motions of the handle to respective corresponding motions of the remote tool.

The professional using the system is able to toggle between the two modes, for example by depressing a trigger incorporated in the handle. The professional is thus single-handedly able operate two separate tools in the procedure using one handle. The system may be easily adapted to operate more than two tools with the one handle, and the system may be used for a variety of different types of tools, such as laparoscopes or graspers.

DETAILED DESCRIPTION

Figure 1:
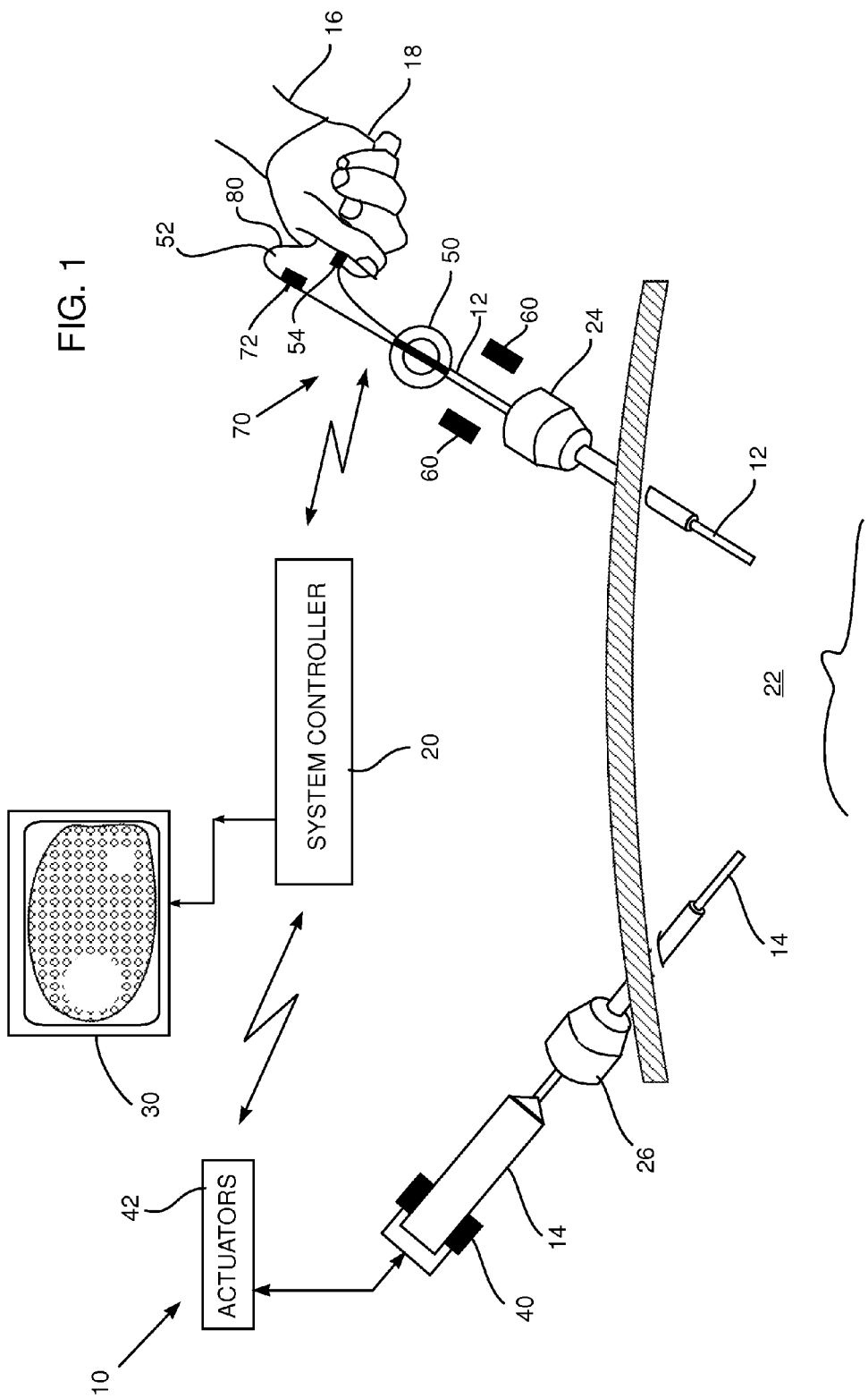
FIG. 1 is a schematic diagram illustrating a relay based tool control system operating in a locked mode, according to an embodiment of the present invention.
Figure 2:
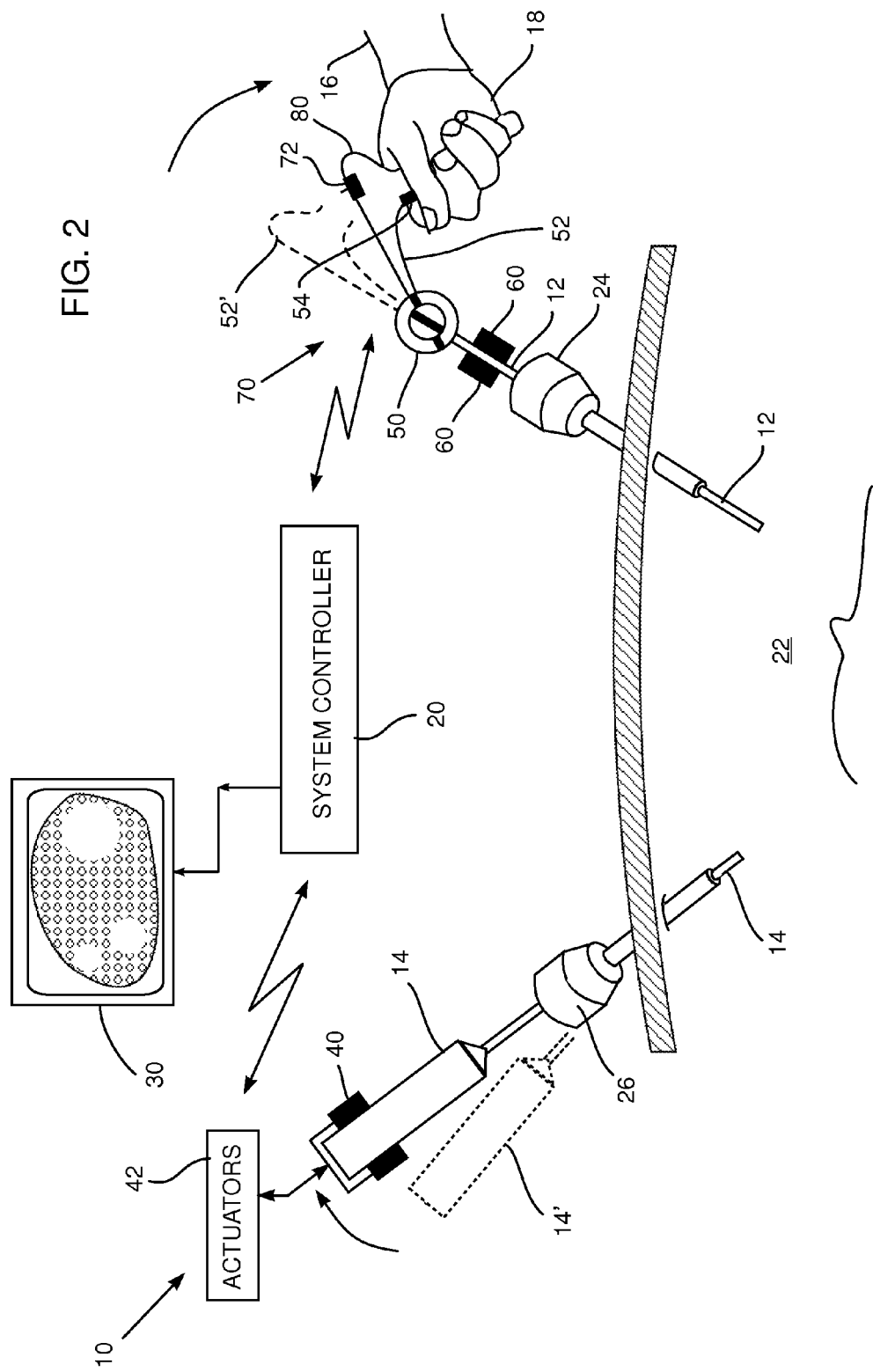
FIG. 2 is a schematic diagram of the relay based tool control system operating in an unlocked mode, according to an embodiment of the present invention.

FIG. 1 is a schematic diagram illustrating a relay based tool control system 10 operating in a locked mode, and FIG. 2 is a schematic diagram of the system operating in an unlocked mode, after transferring from the locked mode, according to embodiments of the present invention. System 10 comprises two medical tools, a local medical tool 12 and a remote medical tool 14. For clarity, in the following description, and except as described below, local tool 12 is assumed to be any tool used in a surgical procedure, such as a retractor or a biopsy tool, and is herein also referred to as hand instrument 12. Remote tool 14 is assumed by way of example to comprise a laparoscope and is also herein termed remotely-operated laparoscope 14 or just remote laparoscope 14. As explained herein, embodiments of the present invention enable both tools to be operated single-handedly by a user 16 of the tools. User 16 is typically a medical professional, and for simplicity, only a single hand 18 of the user, the hand operating the two tools, is shown in the figures.

System 10 includes a system controller 20, which may comprise a general purpose personal computer, and the controller is used to operate other elements of system 10. In order to operate the other elements, the system controller communicates with the elements using wired or wireless transmissions. In the present disclosure, by way of example the communication between the controller and the other elements, or directly between the elements themselves, is assumed to be by wireless transmission.

In operating system 10, user 16 inserts local tool and remote laparoscope 14 into a body cavity 22 via respective trocars 24 and 26 during a medical procedure, so that the two tools are located remotely from each other. In operation, the remote laparoscope acquires an image, which is displayed, under control of system controller 20, on a screen 30. After insertion of the remote laparoscope, the user arranges that the remote laparoscope is gripped by clamps 40. Robotic actuators 42 that control the location and orientation of clamps 40, and thus the location and orientation of remote laparoscope 14, are coupled to the clamps, and the robotic actuators in turn are controlled by system controller 20.

Controller 20 uses software stored in a memory coupled to the controller to operate system 10. Results of the operations performed by controller 20 may be presented to user 16 on screen 30, which typically displays an image of body cavity 22. The software used by the controller may be downloaded to the controller in electronic form, over a network, for example, or it may, alternatively or additionally, be provided and/or stored on non-transitory tangible media, such as magnetic, optical, or electronic memory.

In contrast to remote laparoscope 14, the location and orientation of which is controlled by controller 20, the location and orientation of hand instrument 12 is under the direct control of user 16. In order to achieve such direct control, hand instrument 12 is fixedly connected, via a rotatable, lockable, ball joint 50, to a tool handle 52, also referred to herein as handle 52, which is gripped by hand 18. In a locked mode of operation of system 10 illustrated by FIG. 1, user 16 locks joint 50 so that it is in a locked state, wherein it does not rotate. In this state any movement of the handle is directly transferred to a corresponding movement of the local tool, i.e., hand instrument 12.

By way of example, user 16 is assumed to be able to put system 10 into its locked mode of operation by depressing a trigger 54 in the handle, and by rotating joint 50 so that the handle aligns with local tool 12, at which point the joint locks. As explained below, in this example trigger 54 acts as a toggle switching system 10 between locked and unlocked modes of operation. As for other elements of system 10, trigger 54 is configured to communicate with system controller 20 so that the controller is aware of the mode in which the system is operating. For simplicity, in the remaining description trigger 54 is assumed to be used to toggle between the locked and the unlocked modes of operation. However other methods, such as communicating with system controller 20 with a keypad, a pointing control, a touchpad, another control on handle 52, and/or by non-tactile techniques such as voice actuation, may be used to perform the toggling, and all such methods are within the scope of the present invention.

In the locked mode of operation, clamps 60, which are located in proximity to local tool 12, are positioned by the system controller so as not to interfere with the movement of the local tool actuated by handle 52. (Further functions of clamps 60 are described below.) However, in the locked mode of operation, system controller 20 uses actuators 42 and clamps 40 to maintain remote laparoscope 14 in a fixed location and orientation, so that the image acquired by the remote laparoscope, and displayed on screen 30, does not change.

User 18 toggles system 10 from the locked mode of operation to an unlocked mode of operation, illustrated by FIG. 2, by depressing trigger 54. In entering the unlocked mode system controller 20 unlocks joint 50 so that it is in an unlocked state wherein it is free to rotate. In addition, system controller 20 causes clamps to grip local tool 12, so that the local tool is maintained immobile in a fixed orientation and location, regardless of any rotation or other motion of handle 52 with respect to joint 50.

In the unlocked mode of operation of system 10 a remote tool is manipulated using handle 52, and this mode may also be referred to herein as a remote mode of operation of the system. Similarly, the locked mode of operation of system 10 may also be referred to herein as the local mode of operation of the system.

System 10 comprises sensors 70 which measure motion of the handle with respect to joint 50 when the joint is in its unlocked state. Typically, the sensors detect rotation of handle 52 about joint 50, as well as the equivalent of linear motions of handle 52 with respect to the joint. Typically the sensors detecting rotation measure the rotation in three rotational directions, i.e., pan, tilt, and yaw, and may be installed in joint 50. Sensors measuring the equivalent of linear motion of the handle with respect to joint 50 in three linear directions, may also be installed in the joint. Such sensors typically comprise pressure sensors. Thus, as described in more detail below, pressure by user 16 in a given direction is detected by the sensors and causes a corresponding motion of remote tool 14.

Alternatively, at least some of sensors 70 measuring linear motion may be installed in handle 52. Further alternatively or additionally, at least some sensors 70 may be activated by controls 72, such as sliders, joysticks, or touch sensitive pads, installed in handle and operated by user 16. An example of controls 72 which may be installed in the handle, as well as detail about the controls, is provided below, with reference to FIG. 3A.

In the unlocked mode of operation, measurements of sensors 70 are encoded, and the encoded values are transmitted as signals indicative of the motion of the handle to system controller 20.

System controller 20 uses the encoded values to drive actuators 42, and thus clamps 40, so as to replicate the motions detected by sensors 70. In other words, in the unlocked mode of operation, motions of handle 52 and/or relevant operations of controls 72 are reproduced by corresponding motions of remote laparoscope 14, so that handle 52 effectively acts as a robotic control for the remote laparoscope. For example, as illustrated in FIG. 2, a clockwise rotation of handle 52 from an initial position of the handle shown as a broken outline 52', is replicated by a clockwise rotation of remote laparoscope 14 from an initial position of the laparoscope shown as a broken outline 14'. As a second example, pressure by user 16 in a direction towards joint causes a corresponding "zoom" translation motion of remote laparoscope 14 into cavity 22.

The rotation of the remote laparoscope generates a different acquired image, as is evident by comparison of the images on screen 30 in FIG. 2 and FIG. 1.

Typically, prior to system 10 being used in an operational capacity, there is a calibration stage, calibrating motions detected by sensors 70 with motions produced by remote laparoscope 14.

It will be understood that user 16 may toggle system between the locked and unlocked modes of operation substantially at will, so that the user is able to operate the two separate tools with one hand during the medical procedure referred to above.

For simplicity, the description above has assumed one laparoscope that is operated remotely, in the unlocked mode, by handle 52. However, embodiments of the present invention include operation of more than one remote tool in the unlocked mode using handle 52. In the case of multiple remote tools, which may comprise laparoscopes, each of which is positioned in a respective different location, a selector 80 may be incorporated into handle 52, and user 16 may use the switch to select, at any given time, which of the remote tools is to be controlled by movements of handle 52. A setting of the selector is communicated to system controller 20, which uses the setting to decide which of the remote tools is to be moved.

Figure 3A:
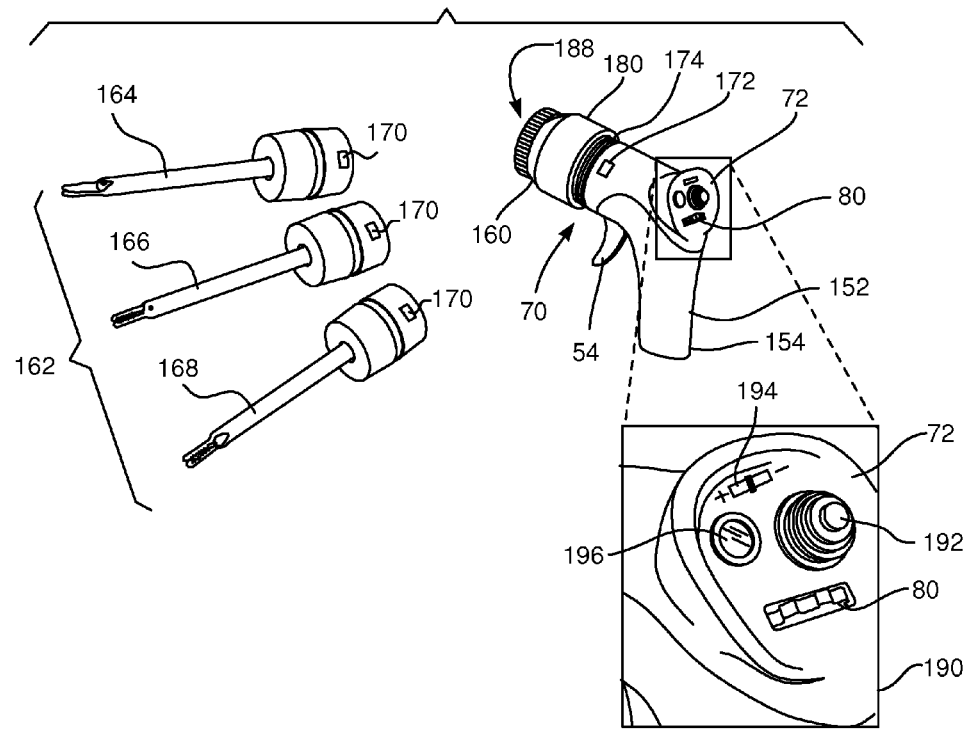
FIG. 3A is a general schematic view of a tool handle.
Figure 3B:
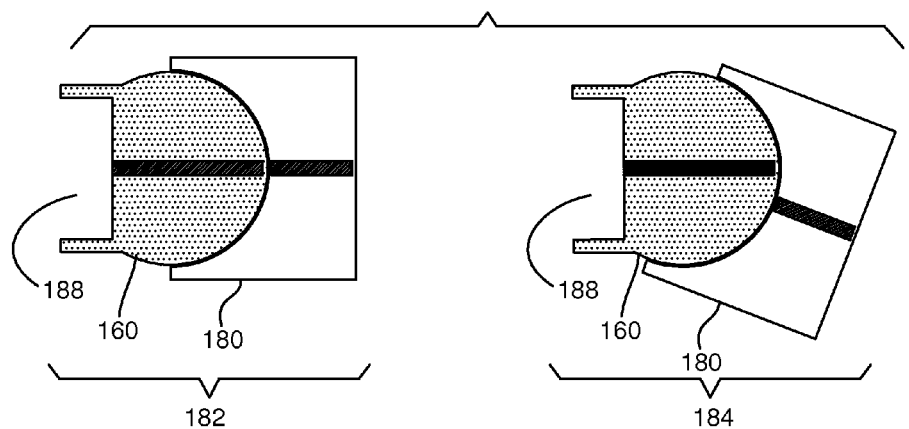
FIG. 3B is a schematic cross-sectional view of a portion of the tool handle.
Figure 3C:
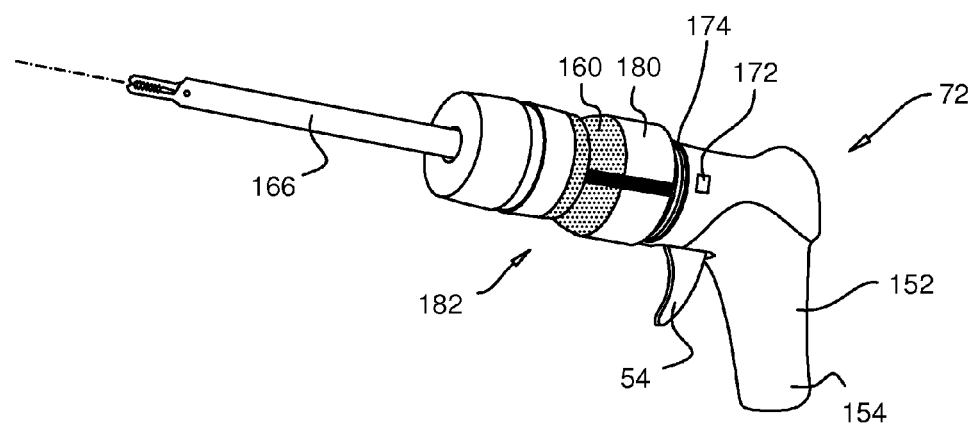
FIG. 3C is a schematic view of the tool handle in a locked mode of operation.
Figure 3D:
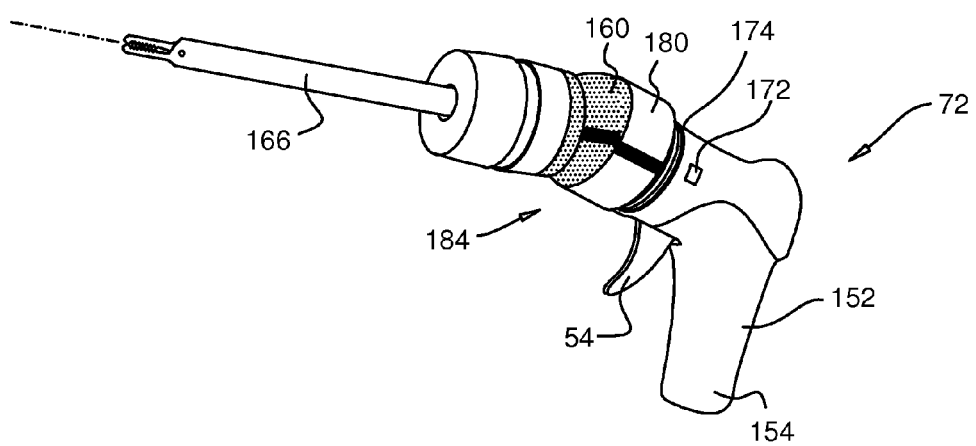
FIG. 3D is a schematic view of the tool handle in an unlocked mode of operation, according to an embodiment of the present invention.

FIG. 3A is a general schematic view of a tool handle 152 and of different local medical tools which may be connected to the handle, FIG. 3B is a schematic cross-sectional view of a portion of tool handle 152 in two different orientations, FIG. 3C is a schematic view of the tool handle in a locked mode of operation, and FIG. 3D is a schematic view of the tool handle in an unlocked mode of operation, according to an embodiment of the present invention. Apart from the differences described below, the operation of handle 152 is generally similar to that of handle 52 (FIGS. 1 and 2), and elements indicated by the same reference numerals in both handles 52 and 152 are generally similar in construction and in operation.

Tool handle 152 comprises a housing 154 which is configured to be gripped by a human hand, so that the housing is typically in the form of a pistol grip. The housing may also be referred to herein as grip 154. In contrast to handle 52, which fixedly connects via joint 50 to hand instrument 12, handle 152 is able to removably connect via a rotatable, lockable, ball joint 160 to any one of a number of different local tools 162 (there are three such tools 164, 166, and 168 illustrated by way of example in FIG. 3A). Examples of tools 162 include, but are not limited to, an endoscope, a grasper, a retractor, and a biopsy tool. Except as described below, joint 160 is generally similar in function and construction to joint 50.

As necessary, one or more linear and/or rotational motors 170 for the operation of local tools 162, typically for implementing physical motion of the distal end of the tools, may be incorporated into the proximal end of the tools. Alternatively or additionally, one or more motors 172 for the operation of the local tools may be incorporated into handle 152, and the movements generated by the motors may be transferred by any suitable means, such as a magnetic linkage, to the tools. Control of motors 170 and/or 172 is described below. For simplicity, the following description assumes motors 170 are in respective tools 162, and those having ordinary skill in the art will be able to adjust the description, mutatis mutandis, for embodiments having one or motors in the handle.

A distal section 180 of handle 152, also referred to herein as joint holding section 180, is configured to accept and retain lockable joint 160. FIG. 3B illustrates two possible orientations of joint 160 with respect to the distal section: a local mode orientation 182 of the joint, where distal section 180 aligns in a locked manner with the joint, and a remote mode orientation 184, where distal section 180 is free to move about the joint. As is also illustrated in FIGS. 3A and 3B, joint 160 comprises, at its distal side, a retaining cup 188, which is configured to accept and hold one of tools 162.

FIG. 3C illustrates handle 152 when joint 160 is locked in local mode orientation 182, so that the handle operates in a local mode. FIG. 3D illustrates handle 152 when joint 160 is unlocked in remote mode orientation 184, so that the handle operates in a remote mode.

As for handle 52, sensors 70 in handle 152 and/or in joint 160 measure motion of handle 152 with respect to the joint when the latter is in its unlocked state. In addition, in the locked state of joint 160, the sensors may be configured to detect adjustments of controls 72, and to apply the detected adjustments to respective motions of the specific local tool 162 connected via retaining cup 188 to joint 160, using motors 170. Typical motions of a local tool, applied using signals from a given sensor, with joint in its locked state, include translation of the distal tip of the local tool in a distal direction. Other motions of the local tool that may be effected when joint 160 is in its locked state are described in more detail in U.S. patent application Ser. No. 13/933,144, referenced above, but for brevity the motions are not described here.

In FIG. 3A an inset 190 is a schematic view of controls 72 that may be mounted on a proximal portion of handle 152. Depending on whether joint 160 is in its locked or unlocked mode of operation, at least some of controls 72, such as the control exemplified below, may operate a local tool or a remote tool.

By way of example, one such control 72 comprises a joystick button 192 which is used to manipulate a distal end of the local or remote tool (according to whether joint 160 is in its locked or unlocked mode) controlled with handle 152. Manipulations that may be implemented using button 192 typically vary according to the type of local or remote tool being controlled, but usually comprise translation of the tool tip, rotation of the tool tip about the distal end axis in a clockwise or counterclockwise direction, and/or bending of the tip from the axis.

A magnification/demagnification regulator 194, comprised in controls 72, also herein termed a mag/demag regulator, enables the user operating handle 152 to set a ratio of movement of another control 72 of the handle, such as joystick button 192, to the actual motion of the local or remote tool coupled to the handle. The ratio may typically be set between a value of 4:1 and a value of 1:4, although other ratios are possible. If set to 4:1, movement of a tool is demagnified by a factor of 4 compared to the movement of the control or action of the handle. If set to 1:4, movement of the tool is magnified by a factor of 4.

For example, with regulator 194 set to a 1:1 ratio, a specific deflection of button 192 may rotate the distal tip of the coupled tool by 30°. If with regulator 194 set to a 2:1 ratio deflection of button 192 rotates the distal tip by 15°.

As stated above, sensors 70 may be used to generate movements of a local tool, or of a remote tool, and the movements may be governed by mag/demag 194. For example, with regulator 194 set to a 1:1 ratio a specific pressure towards joint 160 from grip 154 may be configured to cause, using a given sensor 70, a corresponding translation of the distal tip of the coupled tool by 4 mm. With regulator 194 set to a 2:1 ratio, the same pressure on the sensor causes a translation of 2 mm.

Controls 72 also include one or more indicator lamps 196 and selector 80. Functions of these elements are described in more detail with respect to FIG. 4 below.

Handle 152 has a flexible joint 174 between distal section 180 and housing 154, and the flexible joint is assumed to be included in controls 72. The flexible joint permits relative motion between the housing and the distal section. In the locked mode of operation of handle 152 encoded signals from sensors 70, quantifying the relative motion, may be used to actuate one or more motors 170 of local tool 162 connected to the handle, typically so as to move the distal tip of the local tool according to the relative motion of the flexible joint. In the unlocked mode of operation of the handle the sensor's encoded signals, quantifying the relative motion, may typically be used to move the distal tip of a remote tool being controlled by the handle, according to the relative motion applied to the flexible joint.

Typically, flexible joint 174 may be compressed or expanded linearly and may be configured, using sensors 70, to generate corresponding linear translations of extension or retraction of the distal tip of the local or remote tool being controlled by handle 152. Flexible joint 174 may also be rotated about one or more axes, causing corresponding rotations in the local or remote tool. Motions generated by a flexible joint such as joint 174 are also described in U.S. patent application Ser. No. 13/933,144, referenced above.

FIG. 4 is a schematic illustration of the use of tool handle 152 with local tool 166 during a medical procedure using relay based tool control system 10, according to an embodiment of the present invention. In the procedure, an endoscope 200 has been inserted into body cavity 22, and is held in place by a clamping system 202 to which it is mounted. An additional tool 204 has also been inserted into the body cavity, and is mounted in a clamping system 206. Tool 204 may be generally similar in function and operation to tool 166. Unlike local tool 166, there is no physical connection between the remote tools, i.e. endoscope 200 and tool 204, and tool handle 152. Both clamping systems are adjustable, having movable joints, and the positions and orientations of endoscope 200 and of tool 204 may be modified using their respective clamping systems. Both clamping systems, and consequently tool 204 and endoscope 200, are remotely controlled with actuators, generally similar to actuators (FIGS. 1 and 2). The control is by controller 20, typically using a wireless system. Tool handle 152 is also in communication, typically wireless communication, with controller 20.

Clamps 60 are aligned, and are available for use, with local tool 166. In the local mode of operation of system 10, i.e., when joint 160 is in its locked mode, clamps 60 are disengaged from tool 166, as is illustrated in FIG. 4, and user 16 may move tool 166 with handle 152. In the remote mode of operation of system 10, when joint 160 is in its unlocked mode, clamps 60 engage with tool 166 so that the tool is immobilized.

Endoscope 200 acquires an image of the body cavity, and the image is presented to user 16 on screen 30. Screen 30 shows a distal end of tool 166, and also shows a distal end of tool 204. An alternative presentation of the image acquired by endoscope 200, such as a central portion of the image on screen 30, may be presented to physician 22 on a screen 210 attached to the endoscope.

In some embodiments, user 16 operates a second tool handle 152', which is generally similar in construction and function to tool handle 152. The user may operate tool handle 152 and tool handles 152' at the same time, the simultaneous operation being achieved by the user using his/her right hand to operate tool handle 152, and the left hand to operate tool handle 152'. Operation of tool handle 152' enables the user to operate instruments attached to, i.e., local to, handle 152', as well as instruments remote from handle 152'. Instruments local and remote from handle 152' are different from instruments local and remote from tool handle 152, and it will be understood that by using the two tool handles, a single user 16 may simultaneously manipulate two instruments locally, as well as control one, two, or even more instruments remotely.

In order to operate a remote instrument, user 16 may use controller 20 to call up a selection image 220 on screen 30. The calling up of selection image 220 may be by any convenient method, and herein, by way of example, the user is assumed to use a foot switch (not shown).

Selection image 220 displays a menu of instruments that the user may choose from. By way of example, the menu is shown in iconical form in the figure, but it may also comprise text, or other graphics. FIG. 4 gives as examples an imaging icon 232, a music icon 234, a patient bed icon 236, a remote tool icon 238, a toggle icon 240, and an operating theater illumination icon 242. Imaging icon 232, music icon 234, patient bed icon 236, remote tool icon 238, toggle icon 240, and operating room illumination icon 242 respectively represent endoscope 200, a control for music, a control for the patient bed (not shown), a control for remote tool 204, a toggle control between local and remote modes of operation, the selection of which acts as an alternative to trigger 54, and a control for the operating room lights (not shown). Selection of music icon 234, patient bed icon 236, or illumination icon 242 allows user 16 to operate corresponding facilities of the operating theater.

In addition to the foot switch calling up selection image 220, operation of the foot switch also activates selector 80 (FIG. 3A), herein assumed to be a rotary switch. Rotation of selector 80 sequentially highlights each of the icons of image 220 in turn. To select a particular element represented by an icon, the user stops rotating the selector, and after a preset time, say of 2 seconds, the highlighted element is automatically selected and a lamp 196 flashes to confirm to the user that the selection has been implemented.

Depending on the item selected with selector 80, controller 20 may/may not switch from local to remote operation mode. E.g., if illumination icon 242 is selected, some of controls 72 may be used to change the lights, while the remaining controls may operate as described above for local mode. If selector 80 selects a remote tool, controller 20 toggles to the remote operation mode and controls 72 typically are all directed to operate the selected remote tool. If toggle icon 240 is selected the system may toggle between the remote mode of operation on an already selected remote tool and the local mode of operation on the local tool connected to handle 152.

If the remote tool or element selected is similar to local tool 166, then controls 72 and/or motion of handle 152 with respect to joint 160 may be used to manipulate the remote tool. For example, if selector 80 is used to highlight icon 238, and thus select remote tool 204, the user may be able to use controls 72, rotations about joint 160, and motions with respect to flexible joint 174 to manipulate the distal end of tool 204.

In the case of other remote medical tools or elements that may be selected using selector 80, and that are not similar to a local tool, screen 30 may display functions of controls 72 that correspond to the selected tool or instrument, and also indicate which controls (if any) are not functional. For example, if operating room illumination icon 242 is selected, screen 122 may display that joystick 192 may tilt the operating room lights, and that trigger 54 is not functional.

At any time the user may decouple a remote instrument from controls 72, and recouple the controls to the tool physically connected to handle 152, i.e., to tool 166. The decoupling and recoupling, corresponding to transferring from the remote mode of operation to the local mode of operation, and vice versa, is typically implemented using trigger 54 and/or using selector 80. Alternatively or additionally, the decoupling and recoupling may be implemented using any other method for toggling between two states known in the art.

It will be understood that the scope of the present invention includes medical tools, such as a grasper, a clincher, a biopsy retriever and/or a laparoscope, one of the tools being locally operated in the locked mode of relay based tool control system 10, and one or more other of the tools being remotely operated in the unlocked mode of the system.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising:
providing a local medical tool and a lockable joint connecting between the local medical tool and a handle, wherein the handle comprises at least one sensor;
providing a remote medical tool, located remotely from the local medical tool;
sensing a motion of the handle with the at least one sensor; and
applying indications of the sensed motion to generate a corresponding motion for the remote medical tool when the lockable joint is in an unlocked state,
wherein the at least one sensor is configured to measure a selected motion of the handle with respect to the lockable joint, and the method comprises receiving an indication of the selected motion, and applying the indication to generate a corresponding motion for one of the remote medical tool and the local medical tool.

2. The method according to claim 1, wherein in the unlocked state the local medical tool is immobile.

3. The method according to claim 1, wherein at least one of the medical tools comprises an endoscope.

4. The method according to claim 1, wherein the remote medical tool comprises multiple separate remote medical tools, each separate remote medical tool being located in a respective different position remote from the local medical tool, the method comprising applying the indications to generate the corresponding motion for a selected one of the separate remote medical tools.

5. The method according to claim 1, wherein in a locked state of the lockable joint, movements of the handle are directly transferred to corresponding movements of the local medical tool.

6. The method according to claim 1, wherein the handle comprises controls which, in a locked state of the lockable joint, generate signals used to operate the local medical tool.

7. The method according to claim 6, wherein the controls, in the unlocked state of the lockable joint, generate signals used to operate the remote medical tool.

8. The method according to claim 6, wherein the controls comprise a magnification/demagnification regulator which provides a ratio, the method comprising, in the locked state of the lockable joint, applying the ratio to movements of the handle with respect to corresponding movements of the local medical tool.

9. The method according to claim 8, comprising, in the unlocked state of the lockable joint, applying the ratio to motions of the handle with respect to corresponding motions of the remote medical tool.

10. The method according to claim 1, and comprising connecting a control to the handle, the control providing a motion comprising at least one of a translation and a rotation, and applying the motion of the control to a corresponding motion of one of the remote medical tool and the local medical tool.

11. Medical apparatus, comprising:
a local medical tool;
a remote medical tool, located remotely from the local medical tool;
a lockable joint, physically connected to the local medical tool, operable in a locked state or in an unlocked state;
a handle, physically connected to the lockable joint, so that in the locked state of the joint, movements of the handle are directly transferred to corresponding movements of the local medical tool;

sensors, configured, in the unlocked state of the joint to measure motions of the handle with respect to the lockable joint; and a controller, which in the unlocked state of the joint receives indications of the motions of the handle with respect to the lockable joint, and which is configured to apply the indications to generate corresponding motions for the remote medical tool.

12. The medical apparatus according to claim 11, wherein in the unlocked state the local medical tool is immobile.

13. The medical apparatus according to claim 11, wherein at least one of the medical tools comprises an endoscope.

14. The medical apparatus according to claim 11, further comprising a selector, wherein the remote medical tool comprises multiple separate remote medical tools, each separate remote medical tool being located in a respective different position remote from the local medical tool, and wherein the controller is configured to apply the indications to generate the corresponding motions for one of the separate remote medical tools selected by the selector.

15. The medical apparatus according to claim 11, wherein the handle comprises controls which, in the locked state of the lockable joint, generate signals used by the controller to operate the local medical tool.

16. The medical apparatus according to claim 15, wherein the controls, in the unlocked state of the lockable joint, generate signals used by the controller to operate the remote medical tool.

17. The medical apparatus according to claim 15, wherein the controls comprise a magnification/demagnification regulator which provides a ratio, and wherein the controller, in the locked state of the lockable joint, applies the ratio to the movements of the handle with respect to the corresponding movements of the local medical tool.

18. The medical apparatus according to claim 17, wherein the controller, in the unlocked state of the lockable joint, applies the ratio to the motions of the handle with respect to the corresponding motions of the remote medical tool.

19. The medical apparatus according to claim 11, and comprising a control connected to the handle, the control providing a motion comprising at least one of a translation and a rotation, and wherein the controller is configured, in the unlocked state of the joint to apply the motion of the control to a corresponding motion of the remote medical tool, and in the locked state of the joint to apply the motion of the control to a corresponding movement of the local medical tool.

20. The medical apparatus according to claim 11, wherein the sensors in the locked state of the joint are configured to measure selected motions of the handle with respect to the lockable joint, and wherein the controller receives respective indications of the selected motions, and is configured to apply the respective indications to generate corresponding motions for the local medical tool.

* * * * *